United States Patent
Bailey

[11] Patent Number: 6,146,140
[45] Date of Patent: Nov. 14, 2000

[54] DENTAL PROPHYLAXIS CUP

[75] Inventor: Ronald L. Bailey, Harvester, Mo.

[73] Assignee: Young Dental Manufacturing Company

[21] Appl. No.: 09/348,521

[22] Filed: Jul. 7, 1999

[51] Int. Cl.[7] ............................................. A61C 3/06
[52] U.S. Cl. ................................................... 433/166
[58] Field of Search .................................. 433/166, 125

[56] References Cited

U.S. PATENT DOCUMENTS

| | | | |
|---|---|---|---|
| 2,017,881 | 10/1935 | Wiseman | 433/166 |
| 2,093,006 | 9/1937 | Chott | 433/166 |
| 2,135,933 | 11/1938 | Blair | 601/89 |
| 2,226,145 | 12/1940 | Smith | 15/29 |
| 2,738,528 | 3/1956 | Fridge, Sr. | 15/97.1 |
| 2,789,352 | 4/1957 | Wiseman | 433/166 |
| 3,163,934 | 1/1965 | Wiseman | 433/115 |
| 3,599,333 | 8/1971 | Muhler | 433/166 |
| 4,259,071 | 3/1981 | Warden et al. | 433/166 |
| 4,854,870 | 8/1989 | Kofod | 433/166 |
| 4,929,180 | 5/1990 | Moreschini | 433/166 |
| 5,360,339 | 11/1994 | Rosenburg | 433/165 |
| 5,797,744 | 8/1998 | Rosenburg | 433/166 |

Primary Examiner—John J. Wilson
Assistant Examiner—Melba Bumgarner
Attorney, Agent, or Firm—Polster, Lieder, Woodruff & Lucchesi

[57] ABSTRACT

A prophylaxis cup is provided which has a lower portion and an upper portion. The lower portion of the cup is adapted to mount the cup to a driven member of a prophylaxis angle. The upper portion of the cup includes a wall having an inner surface and an outer surface. The inner surface is smooth and uninterrupted and defines a cavity having a floor and which receives prophylaxis paste. A central post extends up from the cavity floor. A continuous, uninterrupted, circumferential flange extends inwardly from a top of the wall's inner surface. A sloped working surface extends between the flange inner edge and the wall outer surface. The cup is pre-formed to define a flare or annular wedge at the outer edge of the working surface which is sized to permit the working surface to clean a tooth subgingivally and inter-proximally. A generally circular groove on the working surface helps hold the prophy paste. The groove spirals outwardly.

18 Claims, 3 Drawing Sheets

DENTAL PROPHYLAXIS CUP

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

This invention relates to dental prophylaxis (prophy) cups, and in particular to a prophy cup which will more effectively control the pumping or movement of paste from the cavity of the cup.

Rotating prophy cups are generally used both to apply prophy paste to the teeth and to clean and polish the teeth. A prophy cup serves three different functions. It operates as a reservoir which holds prophy paste to be applied to the tooth; it distributes the paste to a working surface of the cup to clean and polish teeth; and it cleans and polishes all surfaces of the teeth, including subgingival and interproximal surfaces of the teeth. Prophy cups typically form a well or cavity into which the paste is inserted, as by dipping the cup in a reservoir of paste. As the cup is rotated by a drive (a prophy angle), the paste exits the cavity and is applied to the tooth. The paste acts as both a lubricant and as an abrasive which removes stains, plaque, and calculus as it is rubbed across the tooth by a working surface of the cup. Presently available prophy cups generally serve well as reservoirs. However, they do not distribute the prophy paste well, nor do they provide large effective working surfaces.

Presently available cups are provided with generally vertical or spiral ribs which are designed to facilitate the cleaning properties of the cups. However, these ribs also facilitate the flow of paste from the cup's cavity. Under the centrifugal forces generated by the cup as it rotates, the paste in the cup cavity quickly exits the cup and splatters on the tooth surface and within the patient's mouth. The cups do not control the flow or exiting of the paste from the cup. The cup, therefore, must frequently be reloaded with paste to perform a single prophy procedure. Further, the quickly diminishing amount of paste present at the interface between the cup and the tooth reduces the amount of abrasion and the cleaning performance of the cup.

When the paste reaches the top surface of the cup, the paste is located primarily in a narrow annular ring, essentially at the edge of the cup. That is, the entire working surface of the cup is not covered with paste. The effective working surface of the cup thus is small.

Cups presently have side walls which are generally straight. Proper cleaning of a patient's teeth requires that the teeth be cleaned subgingivally and interproximally. To clean subgingivally and interproximally with currently available cups, the hygienist must press down on the cup to create a flare which allows the working edge of the cup to penetrate beneath the patient's gum or between the patient's teeth. This requires a fair amount of pressure. Some cups are provided webs which extend inwardly from the inner wall of the cavity. The webs function, in part, to control the amount to which the cup can flare.

Rosenberg, U.S. Pat. No. 5,360,339, attempted to solve some of the problems with distribution of the paste and the working surface of the cup. The Rosenberg cup includes spaced apart ridges or rings on the inner surface of the cup's cavity. The rings are not continuous. Rather, they have aligned gaps formed in them. The rings thus define axial and circumferential channels or grooves. The rings or ridges form the actual working surface of the cup. Thus, the working surface is formed in two discrete annular rings, rather than one large ring. Because the working surface is relatively thick, it may not be able to clean subgingivally or interproximally. Further, it continuously supplies paste to the working surface, rather than supplying the paste only when needed. Rosenberg also provides a flare at the top edge of his cup. However, the flare appears to be too thick to be used either subgingivally or interproximally.

SUMMARY OF THE INVENTION

In accordance with the invention, generally stated, a prophylaxis cup is provided. The prophy cup has lower portion and an upper portion. The lower portion of the cup is adapted to mount the cup to a driven member of a prophylaxis angle. The upper portion of the cup is formed of an elastomeric material, preferably natural rubber, and includes a wall having an inner surface, an outer surface, and a working surface. The inner surface is preferably smooth and uninterrupted and defines a cavity which receives prophylaxis paste. The cavity has a floor. A central post extends up from the center of the cavity's floor. A continuous, uninterrupted, circumferential flange extends inwardly from a top of the wall's inner surface. The working surface extends between the flange's inner edge and the wall's outer surface. The working surface and outer surface define an annular wedge or flare where they join, and which, in cross-section, nearly comes to a point. The annular wedge is sized and shaped to permit the working surface to clean a tooth subgingivally and interproximally with out the need to press down on the cup to create the flare as is needed with currently available prophy cups. Preferably, the wedge ends at a radially outer edge of the cup. The post is shorter than the inner surface of the body upper portion wall such that its top surface is spaced from the bottom surface of the flange. The post defines a truncated cone, and its top surface has a diameter less than the diameter of the inner edge of the flange. The post and flange thus cooperate to define an annular gap. The inner edge of the flange is spaced beneath the outer edge of the cup, and thus, the working surface is sloped. A generally circular groove may be provided on the working surface. The groove is preferably an outwardly spiraling groove. The outer diameter of the upper portion wall increases in diameter from the floor of the cavity to the working surface of the cup. The bottom surface of the flange is shaped to prevent prophy paste from exiting the cup cavity while the cup is spinning and when no side loads are applied to the cup. Preferably, the bottom surface of the flange is flat.

DESCRIPTION OF THE PREFERRED EMBODIMENT

A cup 1 of the present invention is shown in FIGS. 1–4. The cup is made of a pliable elastomeric material having a Durometer hardness of about 40 to about 70. Preferably, the cup is made of natural rubber containing a small amount of mild abrasive. The cup 1, as will be described, is adapted to be removably received on a stem 3 which extends up from a driven member of the prophy angle. The driven member preferably is similar to the driven member shown and described in U.S. Pat. No. 5,730,595 which is incorporated herein by reference. As is known, the driven member, which, for example, may be a gear or a turbine, is rotated by a drive to rotate the cup. The stem 3, shown in FIG. 2 includes a body having splines 5 which radiate outwardly therefrom. A generally cylindrical boss 7 extends upwardly from the stem body above the splines 5 and has a semi-spherical top. There are preferably four splines 5 which are evenly spaced about the stem body, and which are connected by an arcuate surface. That is, there are no sharp corners between the four splines.

Figure 1:
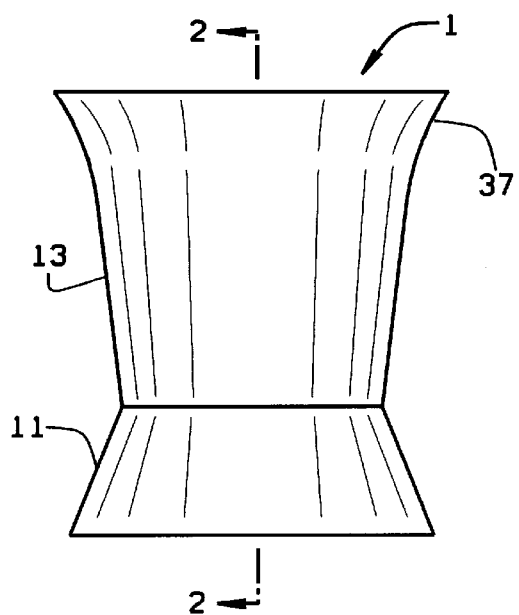
FIG. 1 is an elevational view of a prophy cup of the present invention.
Figure 2:
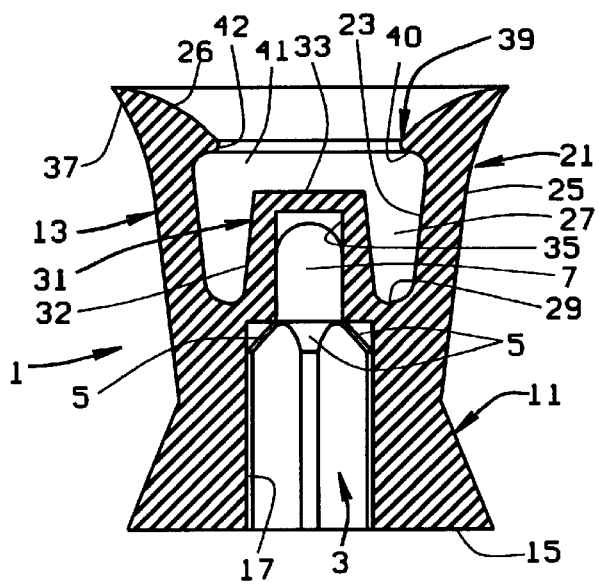
FIG. 2 is a cross-sectional view of the prophy cup taken along line 2—2 of FIG. 1.
Figure 3:
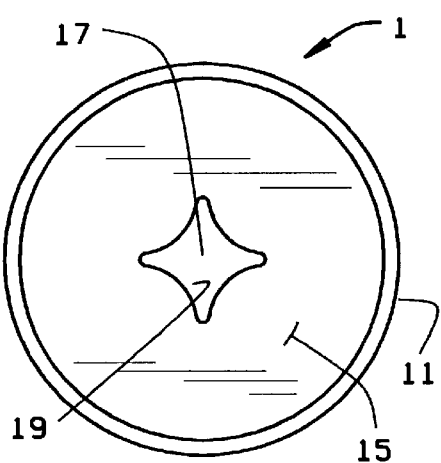
FIG. 3 is a bottom plan view of the prophy cup.
Figure 7:
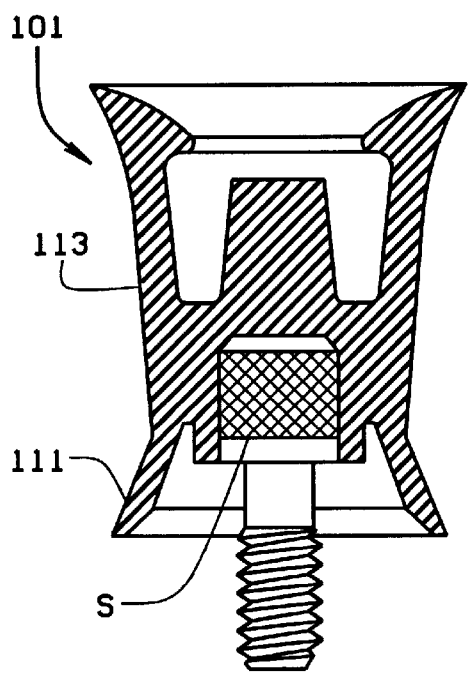
FIG. 7 is a cross-sectional view of an alternate embodiment of the cup, the cup being adapted to receive a screw to secure the cup to a prophylaxis angle.

The cup 1 includes a lower portion 11 and an upper portion 13. The lower portion 11 defines a skirt having a bottom surface 15. As seen in FIG. 2, the skirt is preferably solid, and has a sloped outer surface which slopes downwardly and outwardly, i.e., the diameter at the bottom of the cup is greater than the diameter at the top of the skirt. An opening or bore 17 extends upwardly from the cup's lower surface 15. The opening 17 is sized and shaped to receive the stem 3. As seen in FIG. 3, the opening 17 is formed as a four pointed star or as a square having concave surfaces 19. When the cup is applied to the stem, the surfaces 19 conform to the shape of the stem splines 5 so that a tight interference-type fit is formed between the cup and the stem. This interference-type fit of the cup on the stem will reduce slippage of the cup on the stem, which may occur found in a button-type cup, for example, during a prophylaxis procedure. The cup will actively be driven by the stem, and does not rely on a frictional interaction between the cup and the stem to be spun by the stem. The bottom portion 11 need not be solid, as shown in FIG. 2 or 7. Alternatively, the cup bottom portion 11 could be formed similarly to the bottom portion of the cup shown in U.S. Pat. No. 5,484,248, which is incorporated herein by reference.

The top portion 13 of the cup 1 includes a wall 21 having an inner surface 23, an outer surface 25, and an upper or working surface 26. The inner surface 23 is smooth, uninterrupted, and slopes slightly upwardly and outwardly. That is, the diameter of the inner wall is greater at the top of the wall than at the bottom of the wall. The inner surface 23 of the wall defines a well or cavity 27 having a floor 29. A central spike or post 31 extends up from the center of the floor 29. The post 31 includes a sloped side wall 32 and a flat upper surface 33. The cavity 27 is thus an annular cavity.

The post 31 is designed so that it will remain substantially in one position, i.e., it will not flex substantially when side loads are applied to the cup. The post can be solid (as seen in FIG. 7) or it can have a bore 35 therein which accepts the boss 7 of the stem 3 (as seen in FIG. 2). In either case, the post 31 is preferably integrally formed with the cup and is also made of the same elastomeric material. In the embodiment of FIG. 2, the bore 17 extends through the cup lower portion 11 into the cup upper portion 13 and into the post 31. The stem boss 7 extends into the upper portion 35 of the bore 7 to give the post structural rigidity. If the post 31 is hollow, as shown in FIG. 2, the post's upper surface 33, which is made of rubber, will prevent the stem 3 from contacting the tooth.

Externally, the outer wall 25 is generally smooth and curves outwardly at the top thereof. The working surface 26 and the outer wall 25 together form an annular wedge which defines a flare 37. The flare forms an edge at the top of the cup which is thin enough to enable subgingival and inter-proximal cleaning. Thus, a hygienist will have to apply little or no pressure to the cup to clean subgingivally or inter-proximally.

Figure 4:
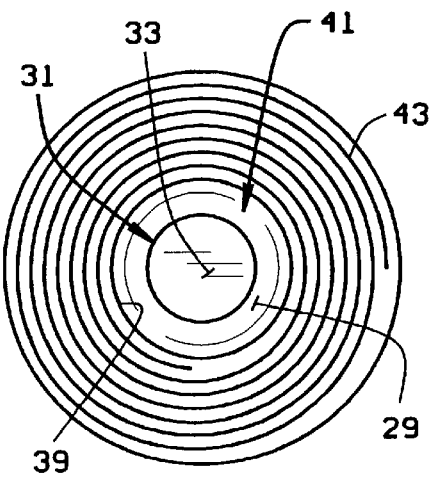
FIG. 4 is a top plan view of the prophy cup.

A flange 39 extends radially inwardly from the top of the inner surface 23 of cup wall 21 to the lower and radially inner edge of the working surface 26. The flange 39 includes a generally flat bottom surface 40 and an inner edge 42. The bottom surface 40 is generally perpendicular to a vertical axis (with reference to FIG. 2) of the cup 1. The bottom surface 40 and edge 42 of the flange 39 are spaced below the top edge of the cup, and the working surface 26 of the cup slopes downwardly and inwardly from the outer surface 25 to the flange edge 42. The bottom surface 40 of the flange is spaced from both vertically and radially from the top surface 33 of the post 31. As noted above, the cup wall 21 slopes diagonally outwardly and the post side wall 32 slopes radailly inwardly. The distance between the post and the inner surface 23 is thus greater at the top of the post than at the bottom of the post. The flange 39 is sized such that there is an annular gap 41, as can be seen in FIG. 4, between the radially inner edge 42 of the flange and the post 31. The post 31 is sized such that its diameter at its top surface 33 is approximately 66% of the diameter of the inner edge 42 of the flange 39.

When the cup 1 is spinning, any paste within the cup will be forced up the wall 23 of the cavity 27 by centrifugal forces. The generally flat and horizontal bottom surface 40 of the flange 39 will substantially prevent the paste from exiting the cup while the cup is spinning and no side loads are applied to the cup. However, as described below, when side loads are applied to the cup, the paste will be pumped or forced from the cavity 27, over the flange edge 42, and onto the working surface 26. Thus, the cup delivers paste only when it is "pumped". The cup will not continuously deliver paste as do presently available cups. The cup therefore will not have to be refilled with paste as frequently during a prophy procedure.

The width of the wall 21 is sufficient to prevent the wall 21 from collapsing under the pressure generally applied to the cup during a prophy procedure. For a cup which has a cavity 27 that is 0.114 inches from the floor 29 to the bottom surface 40 of the flange 39, the wall width is preferably 0.030 inches. The wall 21 has a width that is about 25% of the depth of the well 27.

Figure 8:
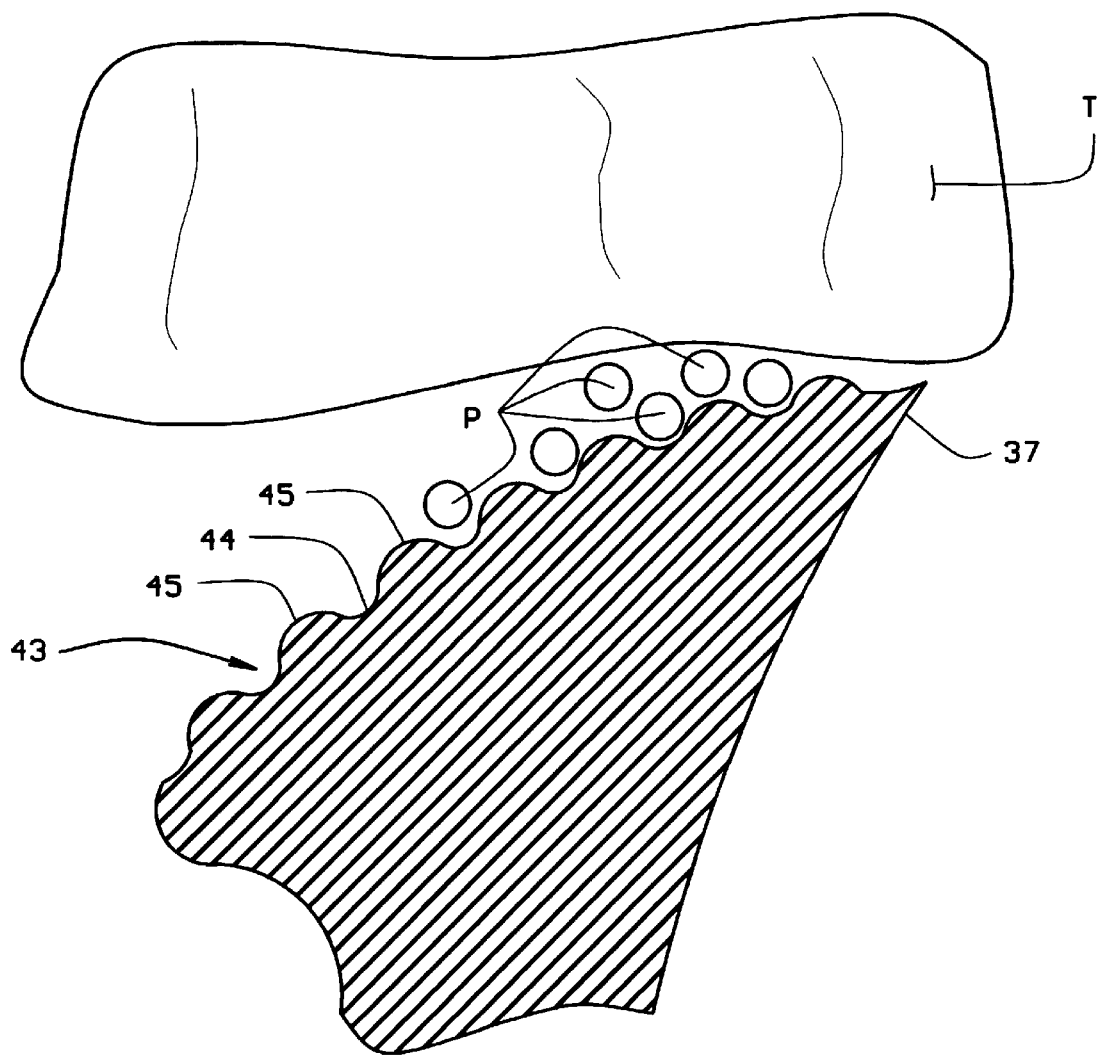
FIG. 8 is an enlarged cross-sectional view of a working surface of the cup applied to a tooth showing a groove in the working surface of the cup.

As seen in FIG. 4, a spiral groove 43 is formed in the working surface 26 of the cup. The groove 43 preferably spirals outwardly from the inner edge 42 of the working surface 26. During use of the cup, the groove 43 helps move new paste to the outer edge of the working surface. Further, the groove 43 creates a larger effective working surface than in prior art cups. The groove 43 traps particles of prophy paste P in the alleys 44 between its ridges 45 and between the ridges 45 and the tooth T, as seen in FIG. 8. This effectively increases the working surface of the cup. In prior cups, the paste is applied only at the periphery of the working surface, whereas, in the cup 1, the paste is applied by a much wider annular portion of the working surface.

Figure 5:
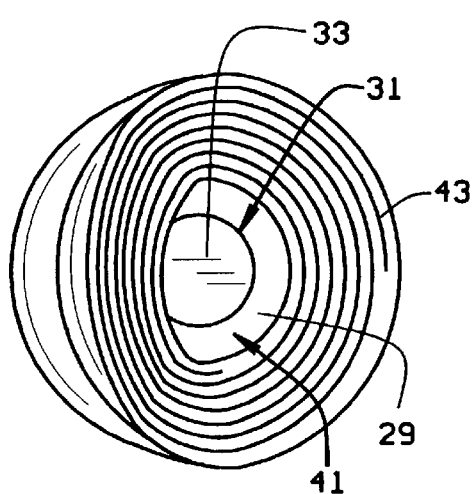
FIG. 5 is a top plan view of the cup when side loads are applied to the cup, as occurs during a prophylaxis procedure.
Figure 6:
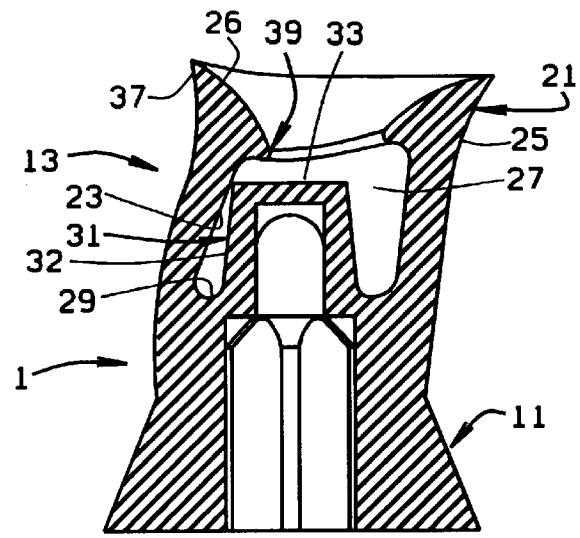
FIG. 6 is a cross-sectional view of the prophy cup of FIG. 5.

When the prophy cup 1 is used in a prophy procedure, the cup is moved sideways over the surface of a tooth T. This movement places a side load on the cup which causes the cup wall to deflect as shown in FIGS. 5 and 6. When the cup wall is deflected, the inner surface 23 of the cup wall 21 will bear against the side surface 32 of the post 31. The gap 41 will thus be effectively narrowed or closed at one point. When the gap is narrowed or closed, the paste in the well 27 will be displaced in the cup and forced over the flange edge 42 and onto the working surface 26 of the cup. Thus, by applying side loads to the cup, the hygienist or dentist will effectively pump prophy paste from the cavity to the working surface of the cup. The pumping of the prophy paste to the working surfaces is controlled by the application of side loads on the cup. When no side loads are being applied to the cup, the paste will not be pumped or otherwise forced from the cup cavity to its working surface. Because the flow of prophy paste from the cavity to the working surface can be controlled, paste can be conserved and there will be less need to replenish the cup during a prophylaxis procedure.

The paste P which is urged onto the working surface will enter the spiral groove 43. The groove will trap the paste on the surface 26 of the cup and allow the paste to move spirally towards the outer edge of the cup surface. The paste will be retained in the alleys 44 and on the ridges 45 of the spiral 43. The spiral ridges will create a better contact of the paste between the cup surface 26 and the tooth T. The alleys 44 of the spiral will control the flow of the paste to the edge of the cup's working surface 26 and will maintain individual particles of paste on the working surface 26 and in contact with the tooth for longer periods of time. This will reduce the amount of splatter of paste in a patient's mouth during a prophy procedure and will form an effectively larger working surface than currently available cups to enable the cup of the present invention to better clean a tooth.

A second embodiment of the cup 101 is shown FIG. 7. The cup 101 has a bottom portion 111 and a top portion 113. The top portion 113 is identical to the top portion 13 of cup 1. The bottom portion has been changed to accept a screw S. This bottom portion is constructed in accordance with that shown and described in U.S. Pat. No. 5,484,284, which is incorporated herein by reference.

As variations within the scope of the appended claims may be apparent to those skilled in the art, the foregoing description is set forth only for illustrative purposes and is not meant to be limiting. For example, the relative dimensions of the post, wall, and flange can be varied if desired to change the ratios noted above. The cup could also be adapted to be a button-type cup, or the cup could be co-molded to a driven member, as is set forth in my above noted co-pending application Ser. No. 632,906, filed Apr. 16, 1996, which is incorporated herein by reference. These examples are merely illustrative.

I claim:

1. A prophylaxis cup for use with a dental prophylaxis angle, the cup including a cup body having a lower portion and an upper portion; said cup lower portion being adapted to mount the cup to a driven member of a prophylaxis angle; said cup upper portion comprising:
   a wall having an inner surface and an outer surface, said inner surface defining a cavity which receives prophylaxis paste, said cavity having a floor, said outer surface extending radially outwardly at the top thereof;
   a central post extending up from said cavity floor, said post having a side wall and a top surface;
   a continuous, uninterrupted, circumferential flange extending inwardly from a top of said wall inner surface, said flange having an inner edge and a bottom surface; and
   a working surface extending between said flange inner edge and said wall outer surface;
   said working surface and outer surface together forming an annular wedge which defines a flare, said flare sized to permit said working surface to clean a tooth subgingivally and interproximally.

2. The prophylaxis cup of claim 1 wherein said inner wall is smooth and uninterrupted.

3. The prophylaxis cup of claim 1 wherein said post upper surface is spaced beneath said flange bottom surface.

4. The prophylaxis cup of claim 3 wherein said post side wall is sloped, said post having a greater diameter at a bottom thereof than at said top surface.

5. The prophylaxis cup of claim 4 wherein the diameter of said post at the top thereof is less than the diameter of the inner edge of said flange, said flange inner edge and said post defining an annular gap.

6. The prophylaxis cup of claim 1 wherein said inner edge of said flange is spaced beneath said outer edge of said working surface, said working surface being sloped.

7. The prophylaxis cup of claim 1 including a generally circular groove on said working surface.

8. The prophylaxis cup of claim 7 wherein said groove is a spiral groove.

9. The prophylaxis cup of claim 8 wherein said groove spirals outwardly toward the outer edge of said working surface, said groove functioning to carry prophylaxis paste in a spiraling manner towards said outer edge of said working surface.

10. The prophylaxis cup of claim 1 wherein the outer diameter of said upper portion wall increases from said cavity floor to the working surface of the cup, said flange bottom surface being shaped to prevent prophy paste from exiting said cup cavity while said cup is spinning and when no side loads are applied to said cup.

11. The prophylaxis cup of claim 10 wherein said flange bottom surface is generally flat and perpendicular to an axis of said cup.

12. A prophylaxis cup for use with a dental prophylaxis angle, the cup including a cup body having a lower portion and an upper portion; said cup lower portion being adapted to mount the cup to a prophylaxis angle; said cup upper portion including:
   a wall having an outer surface and an inner surface, said inner surface being smooth and uninterrupted;
   a cavity defined by said inner surface; said cavity having a floor; said inner surface increasing in diameter from said cavity floor to a top of said inner surface;
   a circumferential flange extending radially inwardly from the top of said wall inner surface; said flange having a bottom surface shaped to prevent centrifugal forces from urging prophy paste out of said cavity while said cup is spinning;
   a working surface extending between an inner edge of said flange and said wall outer surface, said flange inner edge being spaced beneath an upper edge of said outer surface, said working surface being sloped; and
   a spiral groove in said working surface, said groove spiraling outwardly toward an outer edge of said working surface.

13. A prophylaxis cup for use with a dental prophylaxis angle, the cup including a cup body having a lower portion and an upper portion; said cup lower portion being adapted to mount the cup to a driven member of a prophylaxis angle; said cup upper portion comprising:

a wall having an inner surface and an outer surface said inner surface defining a cavity which receives prophylaxis paste, said inner wall being smooth and uninterrupted, said cavity having a floor;

a working surface; and a post extending up from said cavity floor and a circumferential flange extending inwardly from a top of said wall inner surface; said post having a side wall and a top surface; said flange having an inner edge and a bottom surface;

said wall outer surface and working surface together defining a preformed annular wedge ending at a radially outer edge of said cup, said wedge having an outer edge sufficiently thin to permit said working surface to clean a tooth subgingivally and interproximally.

14. A prophylaxis cup for use with a dental prophylaxis angle, the cup including a cup body having a lower portion and an upper portion; said cup lower portion being adapted to mount the cup to a driven member of a prophylaxis angle; said cup upper portion comprising:

a wall having an inner surface and an outer surface, said inner surface defining a cavity which receives prophylaxis paste, said cavity having a floor, said outer surface extending radially outwardly at the top thereof;

a central post extending up from said cavity floor, said post having a side wall and a top surface;

a continuous, uninterrupted, circumferential flange extending inwardly from a top of said wall inner surface, said flange having an inner edge and a bottom surface, and a working surface extending between said flange inner edge and said wall outer surface;

whereby, said circumferential flange substantially prevents prophylaxis paste from exiting said cavity while said cup is spinning and when no side loads are applied to said cup; said cup being operable to deliver prophylaxis paste to said working surface from said cavity when a side load is applied to said cup.

15. The prophylaxis cup of claim 14 wherein said cup post is rigid.

16. The prophylaxis cup of claim 15 wherein said cup post is hollow and defines a chamber, said cup post chamber being adapted to receive a stem from said prophylaxis angle, said prophylaxis angle stem making said cup post rigid.

17. The prophylaxis cup of claim 15 wherein said cup post is solid.

18. A prophylaxis cup for use with a dental prophylaxis angle, the cup including a cup body having a lower portion and an upper portion; said cup lower portion being adapted to mount the cup to a prophylaxis angle; said cup upper portion including:

a wall having an outer surface and an inner surface;

a cavity defined by said inner surface; said cavity having a floor; said inner surface increasing in diameter from said cavity floor to a top of said inner surface;

a post extending upwardly from said cavity floor; and a substantially continuous circumferential flange extending radially inwardly from the top of said wall inner surface, said flange having a bottom surface shaped to prevent centrifugal forces from urging prophy paste out of said cavity while said cup is spinning.

* * * * *